United States Patent [19]

Lin et al.

[11] 4,284,620

[45] Aug. 18, 1981

[54] N-(2-HYDROXYETHYL)-2,4,6-TRIIODO-3,5-BIS-(2-KETO-L-GULONAMIDO)BENZAMIDE AND RADIOLOGICAL COMPOSITIONS CONTAINING SAME

[75] Inventors: Youlin Lin, Chesterfield; Kenneth R. Smith, Black Jack, both of Mo.

[73] Assignee: Mallinckrodt, Inc., St. Louis, Mo.

[21] Appl. No.: 23,506

[22] Filed: Mar. 23, 1979

[51] Int. Cl.$^3$ .......................... A61K 49/04; C07H 5/06
[52] U.S. Cl. ............................................. 424/5; 536/53; 560/251; 564/167
[58] Field of Search .............................. 536/53; 424/5; 260/558 A

[56] References Cited

U.S. PATENT DOCUMENTS

| | | | |
|---|---|---|---|
| 3,666,760 | 5/1972 | Ackerman | 260/558 A X |
| 3,701,771 | 10/1972 | Almen et al. | 260/558 A X |
| 3,770,820 | 11/1973 | Ackerman | 260/558 A X |

FOREIGN PATENT DOCUMENTS

| | | |
|---|---|---|
| 2643841 | 4/1977 | Fed. Rep. of Germany . |
| 7009493 | 12/1970 | Netherlands ................................. 424/5 |

OTHER PUBLICATIONS

Chem. Abstracts 88:23337W.

*Primary Examiner*—Ethel G. Love
*Attorney, Agent, or Firm*—Donald G. Leavitt

[57] ABSTRACT

Novel x-ray contrast agents, i.e., N-(2-hydroxyethyl)-2,4,6-triiodo-3,5-bis-(2-keto-L-gulonamido)benzamide and intermediates.

5 Claims, No Drawings

N-(2-HYDROXYETHYL)-2,4,6-TRIIODO-3,5-BIS-(2-KETO-L-GULONAMIDO)BENZAMIDE AND RADIOLOGICAL COMPOSITIONS CONTAINING SAME

The present invention relates to new compounds, to intermediates for such compounds, to radiological compositions containing such compounds and to the use of such radiological compositions.

Non-ionic contrast agents for intravascular and central nervous system visualization are complex molecules. As is known, the iodine in the molecule provides opacification to the x-rays. The remainder of the molecule provides the frame-work for transport of the iodine atoms. However, the structural arrangement of the molecule is important in providing stability, solubility and biological safety in various organs. A stable carboniodine bond is achieved in most compounds by attaching it to an aromatic nucleus. An enhanced degree of solubility as well as safety is conferred on the molecule by the addition of suitable solubilizing and detoxifying groups.

Several of the features that are desirable for intravascular and central nervous system non-ionic contrast agents are often incompatible so that all such agents represent compromises. In searching for the best compromise, the controlling factors are pharmacological inertness, i.e., in vivo safety, and high water solubility. Thus, the ideal intravascular or central nervous system non-ionic agent represents a compromise in an attempt to obtain the following criteria:

1. Maximum opacification to x-rays
2. Pharmacological inertness
3. High water solubility
4. Stability
5. Selective excretion
6. Low viscosity
7. Minimal osmotic effects An object of the present invention is to provide a non-ionic x-ray contrast agent. Another object of this invention is to provide a non-ionic x-ray contrast agent meeting substantially all the foregoing criteria.

This invention relates to N-(2-hydroxyethyl)-2,4,6-triiodo-3,5-bis-(2-keto-L-gulonamido)benzamide. N-(2-hydroxyethyl)-2,4,6-triiodo-3,5-bis-(2-keto-L-gulonamido)benzamide is subject to a number of different types of isomerism as is explained below. The present invention extends to all isomers thereof having the 2-keto-gulonamido portion in the L form. As used herein, the term N-(2-hydroxyethyl)-2,4,6-triiodo-3,5-(2-keto-L-gulonamido)benzamide means N-(2-hydroxyethyl)-2,4,6-triiodo-3,5,-(2-keto-L-gulonamido)benzamide and all isomers thereof having the 2-keto gulonamido portion in the L form.

This invention also relates to N-(2-acetoxyethyl)-3,5-diamino-2,4,6-triiodobenzamide; 3,5-diamino-N-(2-hydroxyethyl)-benzamide; 3,5-diamino-N-(2-hydroxyethyl)-2,4,6-triiodobenzamide; N-(2-acetoxyethyl)-3,5-bis-(2,3:4,6-di-O-isopropylidene-2-keto-L-gulonamido)-2,4,6-triiodobenzamide; and 3,5-bis(2,3:4,6-di-O-isopropylidene-2-keto-L-gulonamido)-N-(2-hydroxyethyl)-2,4,6-triiodobenzamide, which are intermediates useful in preparing N-(2-hydroxyethyl)-2,4,6-triiodo-3,5-bis-(2-keto-L-gulonamido)benzamide.

N-(2-hydroxyethyl)-2,4,6-triiodo-3,5-bis-(2-keto-L-gulonamido)benzamide exhibits optical isomerism due to the optical characteristics of the sugar amide. In general, the L form of the sugar amide has been used in the present work but the D form can equally be used.

Carbon-13 nuclear magnetic resonance spectroscopy (C-13 NMR) has shown that N-(2-hydroxyethyl)-2,4,6-triiodo-3,5-bis-(2-keto-L-gulonamido)benzamide also exhibits geometrical isomerism of the hemi-ketal bond in the cyclic sugar form. The C-13 NMR spectra reveal that the 2-keto-L-gulonyl portion exists in an α-pyranose form and an α-furanose form in aqueous solution, and that the open chain, the β-pyranose, and the β-furanose forms do not exist in detectable concentrations at room temperature (these forms are illustrated in Table I below). The C-13 NMR spectra also indicate the α-pyranose ring form is the predominant ring form (approximately 90–96%) of the two ring forms and the α-furanose ring form is the minor ring form (10–4%). The chemical shift assignments for the respective carbon atoms are in good agreement with the assignments made by S. J. Angyal and G. S. Bethell, *Australian J. Chem.*, 29, 1249 (1976) for L-sorbose and with those made by T. C. Crawford and G. C. Andrews (Pfizer Laboratories, private communication) for 2-ketogulonic acid (xylo-L-hexulosonic acid) and the methyl ester of 2-keto-L-gulonic acid.

TABLE I

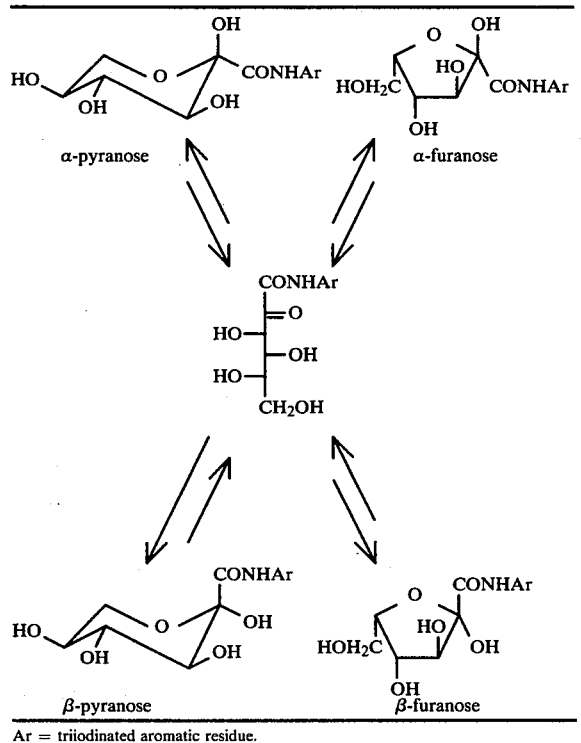

Ar = triiodinated aromatic residue.

Theoretically speaking, N-(2-hydroxyethyl)-2,4,6-triiodo-3,5-bis-(2-keto-L-gulonamido)benzamide can exist as three different isomers at room temperature in water (the existence of an equilibrium between the α-pyranose form and the α-furanose form has not been definitively proven at this time, but most likely there is an equilibrium between the two forms). The three isomers are the: 1) α-pyranose-α-pyranose isomer, 2) the α-pyranose-α-furanose isomer, and 3) the α-furanose-α-furanose isomer. (Naturally trace levels of the open chain, the β-pyranose and the β-furanose forms theoretically would provide twelve additional isomers in solution.)

N-(2-hydroxyethyl)-2,4,6-triiodo-3,5-bis-(2-keto-L-gulonamido)benzamide may be used as an x-ray contrast agent. The agent may be used in various radiographic procedures including those involving cardiography, coronary arteriography, aortography, cerebral and peripheral angiography, arthrography, intravenous pyelography and urography as well as myelography. Mixtures of isomers of this invention may also be used as x-ray contrast agents.

A further feature of the present invention is a radiological composition containing N-(2-hydroxyethyl)-2,4,6-triiodo-3,5-bis-(2-keto-L-gulonamido)benzamide as an x-ray contrast agent together with a pharmaceutically acceptable radiological vehicle.

Pharmaceutically acceptable radiological vehicles include those that are suitable for injection such as aqueous buffer solutions, e.g., tris(hydroxymethyl)amino methane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg. Other buffer solutions are described in *Remingtons Practice of Pharmacy, Eleventh Edition* for example on page 170. The vehicles may contain a chelating amount, e.g. a small amount, of ethylene diamine tetraacetic acid, the calcium disodium salt or other pharmaceutically acceptable chelating agent.

The concentration of N-(2-hydroxyethyl)-2,4,6-triiodo-3,5-bis-(2-keto-L-gulonamido)benzamide in the pharmaceutically acceptable vehicle, for example an aqueous medium, varies with the particular field of use. A sufficient amount is present to provide satisfactory x-ray visualization. For example, when using aqueous solutions for angiography the concentration of iodine is generally 140–400 mg/ml and the dose is 25–300 ml.

The radiological composition is administered so that the contrast agent remains in the living animal body for about 2 to 3 hours, although both shorter and longer residence periods are normally acceptable. N-(2-Hydroxyethyl)-2,4,6-triiodo-3,5-bis-(2-keto-L-gulonamido)benzamide may thus be formulated for vascular visualization conveniently in vials or ampoules containing 10 to 500 ml. of an aqueous solution.

The radiological composition may be used in the usual way in x-ray procedures. For example in the case of selective coronary arteriography, a sufficient amount of the radiological composition to provide adequate visualization is injected into the coronary system and then the system is scanned with a suitable machine, for example a fluoroscope.

N-(2-Hydroxyethyl)-2,4,6-triiodo-3,5-bis-(2-keto-L-gulonamido)benzamide and the intermediates may be prepared in accordance with the procedures set out below. All temperature designations are in degrees centigrade.

EXAMPLE I

Preparation of N-(2-Hydroxyethyl)-2,4,6-triiodo-3,5-bis-(2-keto-L-gulonamido)benzamide (Method A)

A. N-(2-Hydroxyethyl)-3,5-dinitrobenzamide III

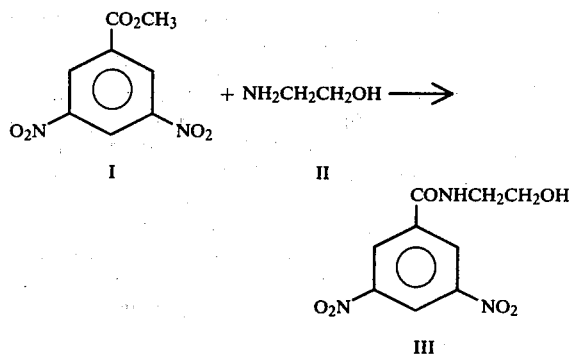

Methyl 3,5-dinitrobenzoate (I, 22.6 g. 0.1 mole) and 50% aqueous 2-aminoethanol (II, 122 g. 2 mole) were placed in a 500-ml flask and the mixture was stirred at room temperature overnight. Water (100 ml) was added and the mixture was stirred for 30 minutes. The crystalline product was collected, slurried in water (100 ml), collected again and dried at 50° under reduced pressure resulting in 22.7 g. of III (0.089 mole, 89% yield). The product showed one spot by tlc analysis in the following two systems: 1. $C_6H_6$/Acetone/AcOH; 90/5/2; 2. EtOAc/MeOH/AcOH; 10/5/1.

NMR data are consistent with the assigned structure III.

B. 3,5-Diamino-N-(2-hydroxyethyl)-2,4,6-triiodobenzamide IV

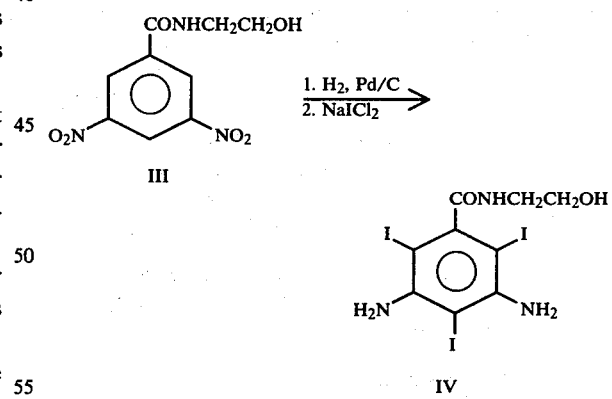

Compound III (127.5 g. 0.5 mole) was suspended in MeOH (1 liter) in a 2-liter reaction bottle under $N_2$; 1% Pd/C (6.59 g) in water (20 ml) was added and the mixture was hydrogenated for 1 day. After filtration the filtrate was placed in a 3-liter flask under $N_2$ and cooled to 5°; $NaICl_2$ (2.3 N, 657 ml, 1.545 mole) was added slowly (40 minutes) so that the reaction mixture was kept below 10°. A tan-colored solid precipitated during the addition of $NaICl_2$. The reaction mixture was stirred at 0°–5° for 3.5 hours and the precipitated solid was collected. The solid was slurried in water (600 ml), collected, slurried in cold (10°) MeOH (480 ml), collected again and air dried to give 271.6 g of IV (0.474 mole, 94.8% yield). The product showed one spot by tlc analysis (C₆H₆/2-butanone/HCO₂H; 70/25/5).

Nmr data are consistent with the assigned structure IV.

C.
N-(2-Acetoxyethyl)-3,5-diamino-2,4,6-triiodobenzamide V

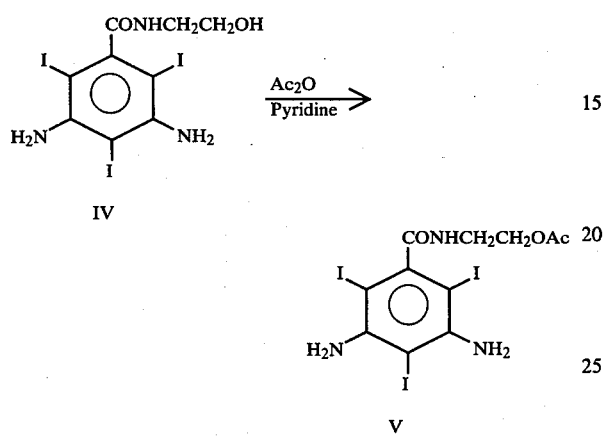

Compound IV (57.3 g, 0.1 mole) was suspended in pyridine (400 ml) and mixed; acetic anhydride (22.44 g, 0.22 mole) was added slowly. The reaction mixture became homogeneous in about 30 minutes and the solution was stirred at room temperature overnight. The solution was then poured slowly into water (3 liters) with rapid stirring which resulted in the precipitation of a white solid. The slurry was stirred for 2 hours and filtered. The solid was washed with water (2 liters) and dried to give 56 g of V (0.091 mole, 91% yield).

Nmr data are consistent with the assigned structure V.

D.
N-(2-Acetoxyethyl)-3,5-bis-(2,3:4,6-di-O-isopropylidene-2-keto-L-gulonamido)-2,4,6-triiodobenzamide VIII

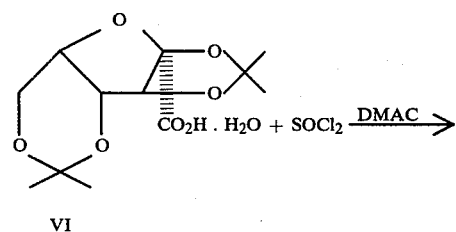

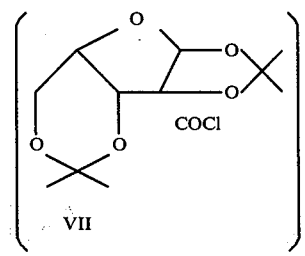

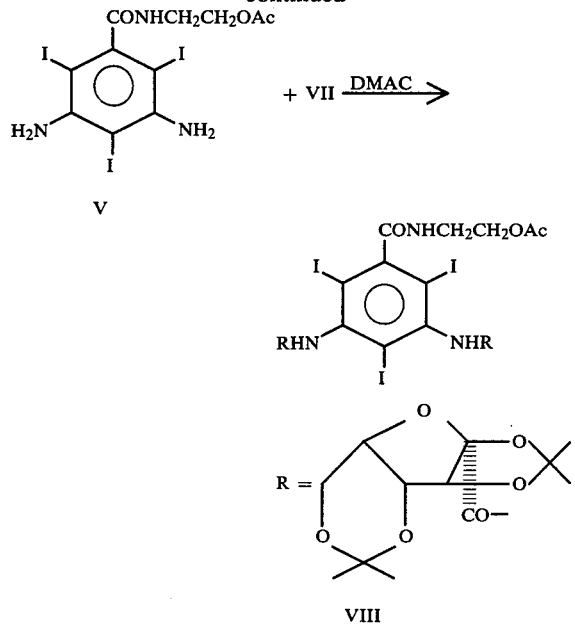

Into a 2-liter flask equipped with a drying tube, a mechanical stirrer and a thermometer, was introduced 2,3:4,6-di-O-isopropylidene-2-keto-L-gulonic acid monohydrate (Hoffman-LaRoche) (compound VI, 101.7 g, 0.348 mole) and N,N-dimethylacetamide (DMAC; 680 ml); the solution was cooled to −10° (methanol-ice bath). Thionyl chloride (74.54 g, 0.626 mole) was added to the solution at such a rate (30 min.) that the reaction temperature remained at 5°-10°. After the addition, the reaction mixture was stirred at −10° for 1 hour, 0° for a second hour and 0°-10° for a third hour.

The solution was then cooled to 0°, compound V (53.5 g, 0.087 mole) was added and the mixture was stirred at 0°-5° for 1 day and at room temperature for 2 days. The reaction mixture was then poured slowly into a stirred solution of 5% NaHCO₃ (3.5 liters). During the addition, CHCl₃ (500 ml) was added to the reaction mixture to prevent foaming. The chloroform layer was separated and the aqueous layer was extracted with chloroform (500 ml×2). The combined chloroform layers were washed with 5% NaHCO₃ (1 liter) and with saturated NaCl solution (1 liter), dried over anhydrous Na₂SO₄ (350 g) and evaporated under reduced pressure to give a glassy residue (102 g). Tlc analysis showed two major spots (in approximately equal quantities), (tlc systems: 1. EtOAc/CH₂Cl₂, 30/20; 2. EtOAc/CHCl₃/AcOH, 30/20/1). A portion (66 g) of the product was used in the following hydrolysis without further purification. A small amount of the product was purified by HPLC and by column chromatography.

Purification of the Product

1. HPLC 5 g of the product was separated on prep LC/System 500 (Waters Associates). The lc conditions were as follows:

| | |
|---|---|
| 1. Sample preparation: | 5g dissolved in 25 ml of CHCl₃/CH₃CN (75/25). |
| 2. Mobile phase: | CHCl₃/CH₃CN (77/23). |

| | |
|---|---|
| 3. Column: | Porasil silica gel |
| Flow rate: | 250 ml/min. |
| Detector: | Model 440 |
| 4. Fractions: | 250 ml. each |

Twenty-four fractions were collected. The first ten fractions were discarded and the remaining fractions were combined and concentrated to give 0.95 g of the desired product VIII as a white, glassy solid. Tlc analysis showed one spot for the product (tlc system: 1. EtOAc/CH$_2$Cl$_2$; 30/20, 2. EtOAc/CHCl$_3$/AcOH; 30/20/1). Nmr data support the assigned structure VIII.

2. Column chromatography 5.5 g of the crude product was dissolved in 20 ml of CHCl$_3$/CH$_3$CN (75/25). The mixture was chromatographed on a column (size: 65×3.5 cm) containing silica gel (330 g, ICN Pharmaceutical) using CHCl$_3$/CH$_3$CN (75/25) as a solvent pair. Fractions 10–21 (50 ml/fraction) were combined and concentrated to give 1.3 g of the desired product VIII.

E.
N-(2-Hydroxyethyl)-2,4,6-triiodo-bis-3,5-(2-keto-L-gulonamido)benzamide IX

Method I

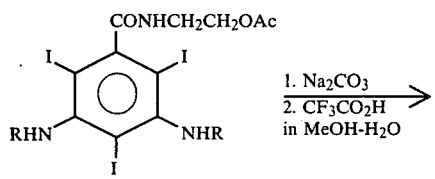

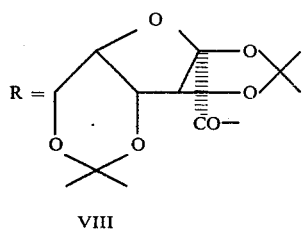

VIII

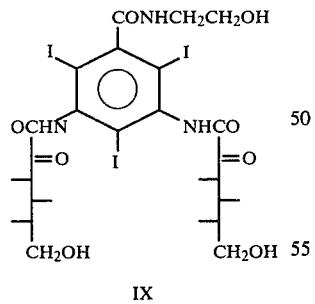

IX

Compound VIII (5.5 g, 4.89 m mole) [obtained from HPLC (3 runs) and from column chromatography (1 run)] was dissolved in MeOH (55 ml) and the solution was diluted with water (55 ml). Anhydrous Na$_2$CO$_3$ (1.04 g, 9.78 m mole) was added, and the solution (pH 11.10) was stirred at room temperature for 2 hours to hydrolyze the acetate protecting group. Trifluoroacetic acid (6 ml) was then added to the solution containing 3,5-bis-(2,3:4,6-di-O-isopropylidene-2-keto-L-gulonamido)-N-(2-hydroxyethyl)-2,4,6-triiodobenzamide, and the solution (pH 0.95) was stirred at 80° (oil-bath) for 18 hours.

The reaction mixture, after cooling to room temperature, was passed through a column containing 150 ml of IR-120 ion-exchange resin (marketed by Mallinckrodt, Inc. under the trade designation Amberlite, 1.75 meq. H$^+$/ml). MeOH—H$_2$O (1:1) was used as the eluent. The fractions which contained the product were evaporated to give a solid (5.5 g). The solid was dissolved in water (100 ml), and the solution was washed with CHCl$_3$/i-PrOH (3:1) (100 ml×2) and evaporated to give a solid. The solid was recrystallized from boiling i-PrOH-absolute EtOH (175 ml/350 ml) and collected (2.3 g). The product was dissolved in water (50 ml), treated with active charcoal (marketed under the trade designation Darco G-60, 100 mg), and the solution was filtered through a 0.22μ filter (marketed under the trade designation Millipore GS). The filtrate was evaporated (reduced pressure, 60°–65°), and the resulting glassy solid was dried at 50° under vacuum overnight to give 2.2 g of IX (2.38 m mole, 48.7% yield). The product showed one spot by tlc analysis (system: 1. CHCl$_3$/MeOH/AcOH; 70/30/2, 2. n-BuOH/H$_2$O/AcOH; 100/30/50). Nmr and ir data of the product are consistent with the assigned structure IX. Elemental analysis: Calcd. for C$_{21}$H$_{26}$I$_3$N$_3$O$_{14}$: C,27.26; H, 2.83; I, 41.15; N, 4.54; Found: C,27.18; H,3.07; I, 41.31; N,4.89

Method II

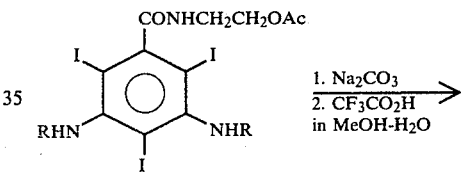

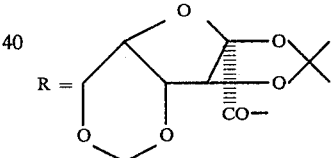

VIII

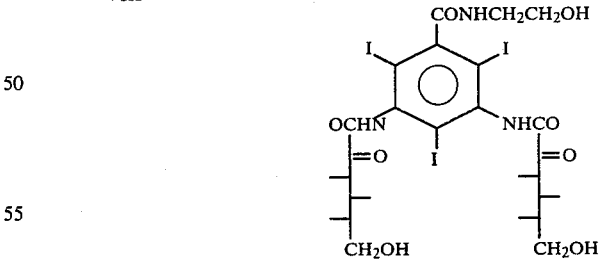

IX

The crude product from Step D (66 g) in MeOH (660 ml) was diluted with water (660 ml) while stirring. Anhydrous Na$_2$CO$_3$ (12.43 g) was added, and the solution was stirred at room temperature for 2.5 hours. The solution was then acidified to pH 1.1 with CF$_3$CO$_2$H (120 ml) and heated to reflux (80° oil-bath) for 16 hours.

The solution was evaporated under reduced pressure at 50° to a volume of 700 ml and was passed through a column (size: 5×20 cm) containing 1 liter of IR-120 ion-exchange resin (marketed by Mallinckrodt, Inc. under the trade designation Amberlite, 1.75 meq. H+/ml), using MeOH—H₂O (1:1) as the eluting solvent. The eluted solution (about 1 liter) was evaporated (55°-60°, reduced pressure) to give a glassy residue. The residue was dissolved in water (500 ml); the solution was washed with CHCl₃/i-PrOH (3:1) (400 ml×2) and evaporated to give a glassy solid (41 g). The material was recrystallized from boiling EtOH/MeOH (550 ml/200 ml) and then from boiling MeOH/EtOH/i-PrOH (300 ml/150 ml/30 ml) to give 12 g of a tan solid. The mother liquor was evaporated to 200 ml to precipitate more product (9.1 g). Both solids showed an identical major and minor spot by tlc analysis (system: 1. CHCl₃/MeOH/AcOH; 70/30/2, 2. n-BuOH/H₂O/AcOH; 100/30/50).

Two more hydrolysis experiments on the crude material from step D provided an additional 44.8 g of the crude product.

Purification of the product by preparative HPLC

The above crude product was purified by preparative HPLC on the prep LC/System 500 (Waters Associates).

The conditions of the lc were as follows:
Column: Prep Pack C₁₈ column.
Detection wavelength: 254 mm.
Chart speed: 0.25 cm/min.
Flow rate: 250 ml/min.
Mobile phase: water.

General Procedure

For each run the crude product (5-6 g) was dissolved in water (25 ml) and injected on the column. The fractions (about 900 ml from each run) containing the major product (the first-eluted component) from 12 runs wee combined and evaporated (50°-60°, reduced pressure). A white glassy solid was obtained, which was dried at 60° under vacuum for 6 hours. The product (31.8 g) was identical to the compound obtained by Method I according to tlc and lc analysis and nmr data.

Tlc analysis showed one spot for the product (system: 1. CHCl₃/MeOH/AcOH; 70/30/2. 2. n-BuOH/H₂O/AcOH; 100/30/50, 3. i-BuOH/i-PrOH/conc. NH₄OH; 10/4/4); analytical lc analysis showed one peak for the product (H₂O as the mobile phase, μC₁₈ column). Nmr data are consistent with the assigned structure IX. The compound softens with darkening at 233°-238° and decomposes above 240°. The compound is highly water soluble (≧100% w/v) and is stable in aqueous solution by tlc and lc analysis.

EXAMPLE II

Preparation of
N-2-(Hydroxyethyl)-2,4,6-triiodo-3,5-bis-(2-keto-L-gulonamido)benzamide (Method B)

A. Preparation of Methyl 3,5-Dinitrobenzoate (I)

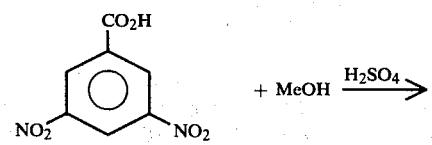

+ MeOH $\xrightarrow{H_2SO_4}$

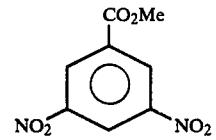

I

In a 72-liter, round-bottomed flask equipped with mechanical stirrer and condenser were combined methyl alcohol (27.97 kg, 873 moles, 35.4 liters), 3,5-dinitrobenzoic acid (15 kg, 70.72 moles), and sulfuric acid (2.6 kg, 26.56 moles, 1.42 liters). The mixture was heated and stirred at reflux by means of a heating mantle for approximately 26 hours and then was allowed to cool to 25° (approximately 18 hours). The precipated solid was isolated by centrifugation (Tolhurst 12-in. centrifuge); each of the four loads collected was washed with methyl alcohol (4 liters). The wet solid was air dried for 16-18 hours to give 14.7 kg (92% of theory) of methyl 3,5-dinitrobenzoate (I). Tlc analysis (toluene/acetone/HOAc; 90/5/2; utilizing a plate marketed by Mallinckrodt under the trade designation ChromAR 7GF plate) showed the product to be homogenous and identical to an authentic sample.

B. Preparation of
N-(2-Hydroxyethyl)-3,5-dinitro-benzamide (III)

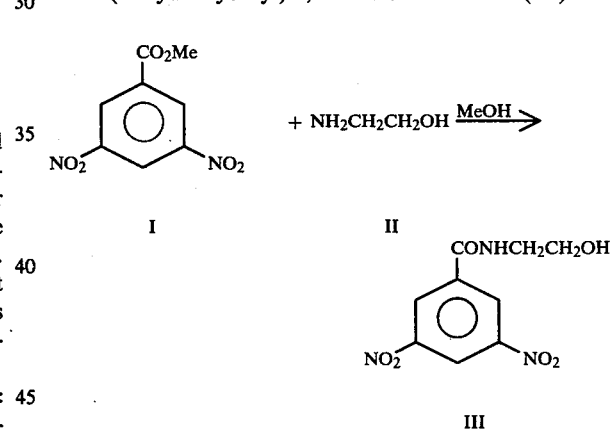

In a 12-liter, round-bottomed flask equipped with a mechanical stirrer, drying tube and thermometer were combined methyl alcohol (3960 ml), 2-aminoethanol (II, 1466.16 g, 24 moles) and methyl 3,5-dinitrobenzoate (I, 2713.68 g, 12 moles) prepared by the procedure set forth in step A. The mixture was stirred without heating for 3 hours during which the temperature rose from 28° to 40° (after 1.25 hours) and then decreased.

After approximately the first half-hour (temp. 34°), the reaction mixture set-up; the mixture was stirred manually until fluid again. After another 20 min. (temp 38°), the mixture set-up a second time and again had to be stirred manually until fluid. The mixture then remained mobile for the remainder of the 3-hour stirring period.

Water (4 liters) was added, and the mixture was stirred for 0.5 hours. The precipitated solid was collected by centrifugation (Tolhurst 12-in. centrifuge) and was washed with water (8 liters). The material was dried for 16-18 hours at 65° to give 2.88 kg (94.8% of theory) of N-(2-hydroxyethyl)-3,5-dinitrobenzamide

11

(III). The material was homogeneous and identical to an authentic sample by tlc analysis (toluene/methyl ethyl ketone/88% formic acid; 70/25/5; utilizing a plate marketed by Mallinckrodt under the trade designation ChromAR 7GF plate).

C. Preparation of 3,5-Diamino-N-(2-hydroxyethyl)benzamide (IIIA) and 3,5-Diamino-N-(2-hydroxyethyl)-2,4,6-triiodobenzamide (IV)

1. Reduction

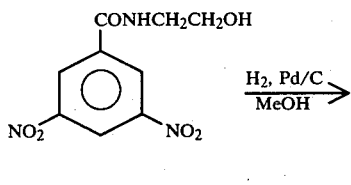

Into a 2-liter Parr shaker bottle was introduced 5% Pd/C (10 g) and N-(2-hydroxyethyl)-3,5-dinitrobenzamide (III, 200 g, 0.79 mole) prepared by the procedure set forth above in step C. The bottle was purged with argon for 10 minutes and methyl alcohol (1.3 liters) was added. The reduction was carried out on a Parr shaker at elevated pressures (20–50 psig) with a total hydrogen uptake of 372 psig (98% of theory) over a 2.66-hour period. The shaker was stopped, and the bottle was left under 50 psig of hydrogen overnight. Tlc analysis (EtOAc/CHCl$_3$/HOAc; 30/20/1; utilizing a plate marketed by Mallinckrodt under the trade designation ChromAR 7GF plate) of the reduction mixture showed one spot (no starting material). The mixture was filtered (to remove the catalyst) into 37% hydrochloric acid (137 ml, containing 59.81 g of HCl, 1.64 moles).

A second identical run was conducted and the two yellowish-green acidified filtrates were combined.

2. Iodination

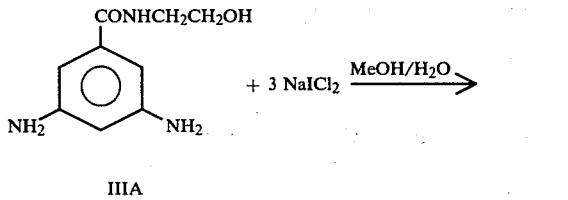

Into a 12-liter, round-bottomed flask equipped with mechanical stirrer, thermometer, and addition funnel was introduced the combined acidified reduction solution of 3,5-diamino-N-(2-hydroxyethyl)benzamide (IIIA, 305.2 g; 1.58 moles) from Part 1. The solution was cooled to 5° in an ice bath, and sodium iododichloride solution (2.016 liters, 2.42 N, 4.88 moles) was added over a 2-hour period keeping the temperature below 10°. The resulting suspension was stirred at 5°–10° for 2 hours, and then was allowed to warm slowly to room temperature (i.e. as the ice bath melted). After the reaction mixture was stirred overnight at room temperature, the precipitated solid was collected and washed with water (3.0 liters). The material was slurried in methyl alcohol (1.5 liters) for 20 minutes, collected and air dried to give 838.92 g (98.5% of theory) of 3,5-diamino-N-(2-hydroxyethyl)-2,4,6-triiodobenzamide (IV) as a yellowish-tan solid.

Tlc analysis (EtOAc/CHCl$_3$/HOAc; 30/20/1; utilizing a plate marketed by Merck under the trade designation Silica 60 F-254 plate) showed the product to be homogeneous and identical to an authentic sample. Lc analysis showed the product purity to be greater than 98%.

D. Preparation of N-(2-Acetoxyethyl)-3,5-diamino-2,4,6-triiodobenzamide (V)

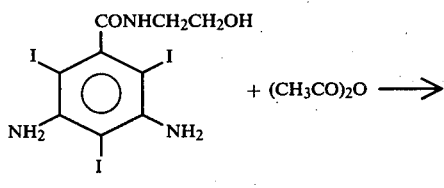

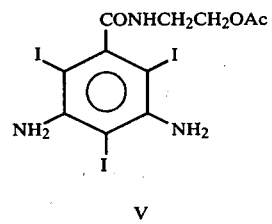

Into a 5-liter, round-bottomed flask equipped with mechanical stirrer, thermometer, addition funnel and drying tube was introduced 3,5-diamino-N-(2-hydroxyethyl)-2,4,6-triiodobenzamide (IV, 573 g, 1.0 mole; prepared by the procedure set forth in step D above) and pyridine (3.4 liters). To the stirred suspension was added acetic anhydride (224.6 g, 2.2 mole, 208 ml) via the dropping funnel over a 40-minute period. The temperature rose from 24° to 30°, and all solids dissolved within 20 minutes after the addition was complete giving a dark solution. The mixture was stirred at room temperature for 23 hours. The dark, homogeneous reaction mixture was poured into water (14 liters) with rapid stirring. After being stirred for 1.5 hour, the suspension was filtered and the collected solid was washed with water (2 liters). The material was air dried several days and then further dried in vacuo at 25° overnight to give 602.18 g (98% of theory) of N-(2-acetoxyethyl)-3,5-diamino-2,4,6-triiodobenzamide (V) as a yellowish-tan solid.

A second large scale preparation utilizing the same procedure gave 515.4 g (97% of theory) of the acetate diamine (V). Tlc analysis (EtOAc/CHCl$_3$/HOAc;

30/20/1; utilizing a plate marketed by Merck under the trade designation Silica 60 F-254 plate) showed the product to be homogeneous. Karl-Fisher analysis showed 0.71% water present in the product.

E. Preparation of Sodium 2,3:4,6-Di-O-isopropylidene-2-keto-L-gulonate (VIA)

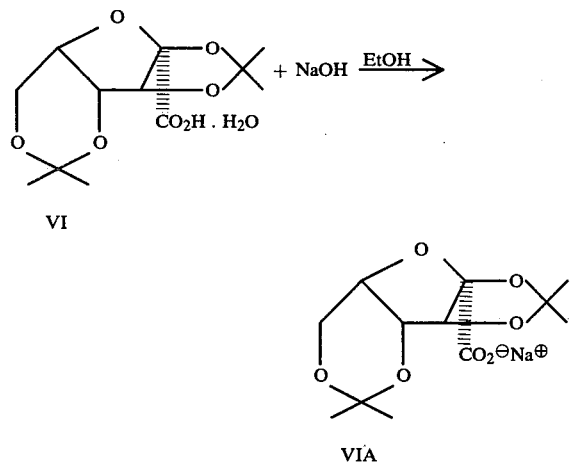

Into a 12-liter, round-bottomed flask equipped with a mechanical stirrer was added sodium hydroxide (204 g, 5.1 moles) and ethyl alcohol (9.0 liters). The mixture was stirred for approximately 1 hour until the sodium hydroxide dissolved. 2,3:4,6-Di-O-isopropylidene-2-keto-L-gulonic acid monohydrate (VI; 1490.6 g, 5.1 moles) was added and quickly dissolved. After 1 hour a heavy precipitate formed; stirring was continued for approximately 19–20 hours. The suspension was concentrated in vacuo; the residue was spread on trays and dried at 70° C. overnight. The product was pulverized into a powder which was redried at 70° overnight to give 1.5 kg (99% of theory) of sodium 2,3:4,6-di-O-isopropylidene-2-keto-L-gulonate (VIA).

F. Preparation of 2,3:4,6-Di-O-isopropylidene-2-keto-L-gulonyl Chloride (VII)

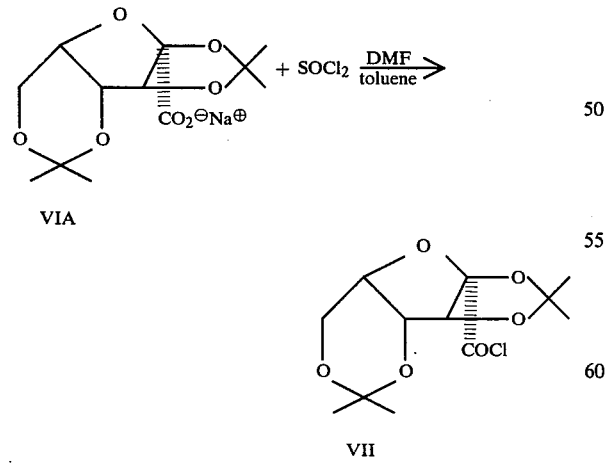

(a) Into a 12-liter, round-bottomed flask equipped with a mechanical stirrer, thermometer, Dean-Stark trap and condenser was introduced sodium 2,3:4,6-di-O-isopropylidene-2-keto-L-gulonate (VIA; 600 g, 2.03 moles; prepared by the procedure set forth above in step E) and toluene (6.0 liters). The slurry was heated to reflux by means of a heating mantle and water and ethyl alcohol in the sodium salt was removed by azeotropic distillation of the toluene (1.45 liters) through the Dean-Stark trap. The slurry was allowed to cool to 37°, and thionyl chloride (356.6 g; 3.0 mole; 217.6 ml) was added over a 15-minute period via a dropping funnel. The temperature rose to 46° during the addition. N,N-Dimethylformamide (DMF; 14.6 g; 0.2 mole, 15.5 ml) was added in one portion, and the mixture was stirred and heated at 50° for 2.5 hours during which the salt dissolved, giving a pale yellow solution. The reaction mixture was concentrated in vacuo at 50° (water bath). The residue was slurried in petroleum ether (30°–75°; 5.0 liters) for 2.5 hours. The resulting slurry was filtered (to remove sodium chloride) and the filtrate was concentrated in vacuo at 50° (water bath) to an orange oil which was dried further under high vacuum for approximately 22 hours to give 522.11 g (88% of theory) of 2,3:4,6-di-O-isopropylidene-2-keto-L-gulonyl chloride (VII) as an oil which had a putrid odor. The ir spectrum was consistent with the assigned structure.

In addition to the above run, three other large scale preparations of the acid chloride were conducted as follows: B, 259.1 g, 88.5%, C 246.7 g, 83%; and D, 534.13 g, 90%.

G. Preparation of N-(2-Acetoxyethyl)-3,5-bis-(2,3:4,6-di-O-isopropylidene-2-keto-L-gulonamido)-2,4,6-triiodobenzamide (VIII)

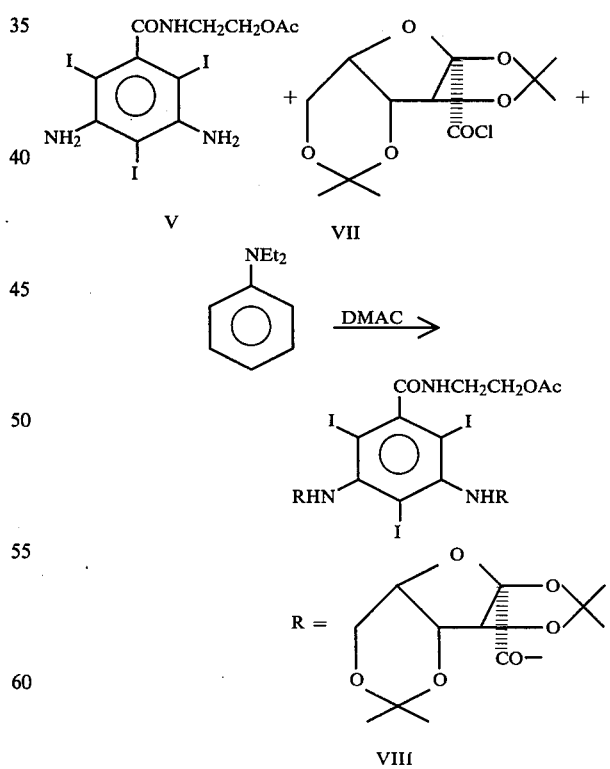

Into a 2-liter, three-necked, round-bottomed flask equipped with stirring bar (magnetic stirrer), thermometer, dropping funnel and drying tube were introduced 2,3:4,6-di-O-isopropylidene-2-keto-L-gulonyl chloride (VII, 259.1 g, 0.885 mole; prepared in the same manner set forth above in Step F) and N,N-dimethylacetamide (DMAC; 574 ml). N-(2-Acetoxyethyl)-3,5-diamino-2,4,6-triiodobenzamide (V, 164.9 g, 0.268 moles; prepared in the same manner set forth above in step D except for reagent quantities) and N,N-diethylaniline (79.98 g, 0.536 moles, 86 ml; via the dropping funnel) were added simultaneously over a 4-minute period to the stirred solution. After being stirred for 16 minutes, all solids dissolved giving a very dark purple solution. After the addition was complete, the temperature rose from 25° to 33° over a 46-minute period and then decreased. After being stirred at room temperature for 19 hours, the reaction mixture was yellowish-brown. After another 24 hours, lc analysis showed the reaction to be complete.

The reaction mixture was poured into a stirred slurry of sodium bicarbonate (150 g) and water (580 ml); a gum formed, so chloroform (1.5 liter) was added. The mixture was stirred 20 minutes; the organic layer was separated, and the aqueous layer was stirred with a second portion of chloroform (1 liter) for 10 minutes. The combined chloroform extracts were washed with 5% aqueous sodium bicarbonate (1×1 liter), water (1×1 liter), 10% hydrochloric acid (3×1 liter) and water (1×1 liter). The organic layer was stirred with sodium sulfate overnight, and then after filtration, was concentrated in vacuo (50° water bath) to a dark oil which was further dried under vacuum for 10 hours to give 330.6 g (109% of theory; DMAC still present) of N-(2-acetoxyethyl)-3,5-bis-(2,3:4,6-di-O-isopropylidene-2-keto-L-gulonamido)-2,4,6-triiodobenzamide (VIII) as a yellowish-tan, foam-like solid which had a putrid odor.

Lc analysis showed three or four minor impurities; the nmr spectrum was consistent with the assigned structure (VIII).

Three other condensation runs also gave yields in excess of theory and all products were of similar purity by lc analysis.

The weights and moles of acetate diamine (V) and weights of (VIII) obtained with the theoretical yields are given below for the other three condensations:

| V ACETATE DIAMINE USED (MOLES) | VII GULONYL CHLORIDE USED (MOLES) | VIII OBTAINED (THEORETICAL YIELD) |
|---|---|---|
| 134.55g (0.218) | 211.4g (0.72) | 274.2g (245.78g) |
| 326.4g (0.53) | 512.9g (1.75) | 691.19g (597.55g) |
| 332.3g (0.54) | 522.1g (1.78) | 739.0g (608.83g) |

H. Preparation of N-(2-Hydroxyethyl)-2,4,6-triiodo-3,5-bis-(2-keto-L-gulonamido)benzamide (IX)

1. Hydrolysis

There were three separate hydrolysis experiments conducted; one of these will be described in detail, then the results of the other two experiments are included.

a. First Experiment

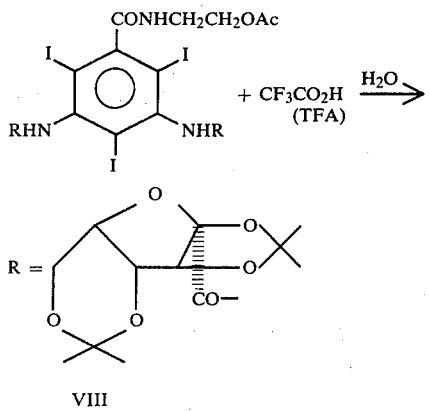

To a 12-liter, three-necked, round-bottomed flask equipped with a mechanical stirrer, condenser, and thermometer were added N-(2-acetoxyethyl)-3,5-bis-(2,3:4,6-di-O-isopropylidene-2-keto-L-gulonamido)-2,4,6-triiodobenzamide prepared in the same manner as set forth above in step G, [VIII, (739 g, crude wt. used); (608.83 g, 0.540 moles; theoretical wt.)] and water (6.57 liters). The system was put under a static nitrogen atmosphere; trifluoroacetic acid (373.71 g, 3.28 moles, 243.5 ml) was added, and the stirred mixture was heated to 80° using a heating mantle. At approximately 48°, all of the solid turned to a gum which stopped the stirrer. The stirrer was turned manually until the temperature rose a few degrees at which point the gum broke-up and the stirrer started again. The mixture became homogeneous at 78°–80°. The progress of the reaction was followed by lc and tlc (n-BuOH/H$_2$O/HOAc; 100/30/50; utilizing a plate marketed by Mallinckrodt under the trade designation ChromAR 7GF plate). The reaction was complete after 2 hours at 80°; the amber reaction mixture was concentrated in vacuo (60°–70° water bath). The residue was dried under high vacuum overnight to give 704.44 g (theoretical yield=499.56 g) of crude IX as a yellow, foam-like solid. Lc analysis H$_2$O; μC$_{18}$, flow-1 ml/min., chart-0.1 in/min.) showed an impurity at the solvent front (probably colored impurities) and two others with retention times of 10 and 27 minutes; tlc analysis (system and plate as before) showed two minor higher R$_f$ impurities.

b. Second Experiment Results

VIII, [563.91 g (crude wt. used), (512.81 g, 0.455 moles (theoretical wt.)] gave 521.42 g (theoretical yield420.94 g) of crude IX; reaction time—3 hours (monitored by lc); lc and tlc analysis of the final product gave similar results as for (a) above.

c. Third Experiment Results

VIII, [691.0 g (crude wt. used); (597.55 g, 0.53 moles (theoretical wt.)] gave 665.5 g (theoretical yield-490.33 g) of crude IX; reaction time—5 hours (monitored by lc); lc and tlc analysis of the final product gave the same results as in the other two runs.

2. PURIFICATION

The crude products from the hydrolysis experiments (a) and (b) were combined for purification. The crude product from (c) was purified separately.

(a)

Crude IX [704.44 g from experiment (a) and 505.38 g from experiment (b)] were combined (1209.82 g) and dissolved in 6.05 liters of methyl alcohol at 55°–60°. This hot solution was added over a one-hour period to a stirred solution of isopropyl alcohol (12.1 liters) at 67°. The resulting slurry was stirred and allowed to cool to 25° overnight. The suspended solid was collected, washed with a 2:1 mixture of isopropyl alcohol and methyl alcohol (2.5 liters), and sucked partially dry to give 1676 g of damp cake (a). A LOD on 40 g of the damp cake (25° under vacuum) showed the material to be approximately 48% solids or 804.48 g.

The damp material was taken up in methyl alcohol (6 liters) at 65°. This hot solution was added over a 20-minute period to a stirred solution of isopropyl alcohol (12 liters) at 67°. The resulting suspension was stirred and allowed to cool to 25° overnight. The solids were collected, washed with a 2:1 mixture of isopropyl alcohol and methyl alcohol (2.5 liters), and sucked partially dry to give 1442 g of damp cake (b).

The damp cake (now 1367 g; wt. reduced by air drying; LOD showed 50% solids or 683.5 g) was dissolved in 6.87 liters of 0.01 N sodium hydroxide. The solution was stirred at room temperature for two hours and then was stirred with a Barnstead mixed bed resin (2,734 kg; Code D0809; prewashed with deionized water) for 1 hour. The resin was removed by filtration and was washed with several liters of deionized water.

The resulting solution had a pH of 4.81. The solution was treated twice with charcoal (marketed under the trade designation Darco G-60; 34 g each time) for 0.5 hours and 0.75 hours respectively. After the first charcoal treatment, the solution pH was 5.36, and then it dropped to 4.81 after the second treatment.

The solution was stirred again with Barnstead mixed bed resin (683 g) for approximately 1 hour. The resin was filtered off and thoroughly washed. The solution pH now was 5.58. Another treatment with charcoal (marketed under the trade designation Darco G-60, 34 g) for 40 minutes resulted in a colorless solution (pH: 5.4), which was filtered through a 0.22μ filter pad (marketed under the trade designation Millipore-Type GS). This solution was then combined with the final solution from Part 2-b.

(b)

The crude product from experiment c (665.5 g) was crystallized from methyl alcohol (3.3 liters)-isopropyl alcohol (6.6 liters) at 60°–65° (addition time—0.5 hours) as described in Part 2-a to give 912.23 g of damp cake (C). This material was crystallized again from methyl alcohol (3.76 liters) and isopropyl alcohol (7.53 liters) at 60°–68° (addition time—2 hours). In this case, the resulting suspension was stirred at 50°–60° for 20 minutes and filtered hot. The cake was washed as usual and sucked dry overnight to give 382.3 g of slightly damp cake.

The damp cake (382.3 g) was dissolved in 0.01 N sodium hydroxide (3.8 liters). The amber colored solution was stirred at room temperature for 3.5 hours and then was stirred with a mixed bed resin (1.14 kg; marketed under the trade designation Barnstead, Code D0809, prewashed with deionized water) for 1 hour. The resin was filtered off and thoroughly washed. The resulting yellow solution (pH: 4.0) was treated with charcoal (marketed under the trade designation Darco G-60; 19 g) for 0.5 hours giving a greenish-colored solution with a pH of 4.8. The solution was again stirred with the mixed bed resin (380 g) for 0.5 hours. After removal of the resin, the solution (pH: 5.4) was treated twice with 19 g portions of the above mentioned charcoal for 0.5 hours each time (pH: 5.2 after first treatment, pH: 5.07 after second treatment). The resulting colorless solution was filtered through a 0.22μ filter pad (marketed under the trade designation Millipore Type GS).

c. Isolation of the COMPOUND IX

The solutions from parts 2-a and 2-b were combined and concentrated in vacuo (vacuum pump; 50° water bath). The off-white, glass-like solid residue was dried at room temperature under high vacuum for 2.5 days to give 755.84 g of IX. Karl Fisher analysis showed 4.65% water; therefore, the dry yield was 720.69 g [50% of theory from the acetate diamine (V)]. The material was pulverized and dried an additional 5.5 hours under house vacuum at 60° to give a final water content of 3.58%.

Analytical Data: (1) Lc analysis (μC$_{18}$ column, water mobile phase, flow-1 ml/min.) showed the product to be about 98% pure. The retention time for IX is 5.75 minutes; (2) Tlc analysis (n-BuOH/H$_2$O/HOAc; 100/30/50; utilizing a plate marketed by Mallinckrodt under the trade designation ChromAR 7GF plate) showed one spot with a R$_f$ of 0.42; (3) pH of a 5% solution: 5.0; (4) M.P. 195° (soften), 206° (sl. discoloration), 218°–222° (dec.); (5) solubility—100% (W/V); (6) the ir and pmr spectra were consistent with the assigned structure. Elemental analysis; Calcd for C$_{21}$H$_{26}$I$_3$N$_3$O$_{14}$ (after correction for 3.58% H$_2$O): C, 26.29; H, 3.13; I, 39.67; N, 4.38; Found: C, 26.20; H, 3.12; N, 4.09; I, not determined.

EXAMPLE III

A female mouse (19 g) was anesthetized with sodium pentobarbital (60 mg/kg, i/p.). N-(2-Hydroxyethyl)-2,4,6-triiodo-3,5-bis-(2-keto-L-gulonamido)benzamide prepared according to Method A 10,000 mg I/kg (37% I solution), I.V., was injected via a lateral tail vein at a rate of 2 ml/minute. A whole body left lateral radiograph with good visualization of the vascular system was taken 5 seconds after administration.

Similar posteroanterior radiographs were obtained 30 seconds and 5 minutes after contrast administration with good images of the vascular and urinary systems respectively.

A pentobarbital-anesthetized rat (233 gm) received 175 mg I/kg (37% I solution) of the compound intracisternally. Lateral radiographs of the head and thorax were obtained 10 seconds after contrast administration with good visualization of the subarachnoid space in the upper cervical, cisternal and basal cistern regions.

EXAMPLE IV

The following pharmacological studies were run on the N-(2-hydroxyethyl)-2,4,6-triiodo-3,5-bis-(2-keto-L-gulonamido)benzamide prepared according to Method B (PRODUCT).

1. Acute Intravenous Toxicity in Mice

A solution of the PRODUCT was injected into the lateral tail vein of yound adult male and female Swiss mice at a rate of 1 ml/min. Following injections, the animals were observed for immediate reactions and then daily throughout a seven day observation period. The $LD_{50}$ values were calculated by the method of Litchfield and Wilcoxon (J. Pharmacol. Exp. Therap. 96: 99–113, 1949) with the following results.

| Concentration | $LD_{50}$/(95% Confidence Limits) | |
| (mg I/ml) | mg I/kg | mg/kg |
| --- | --- | --- |
| 400 | 18,200 (16,499–20,075) | 44,228 (40,094–48,785) |

2. Acute Intracerebral Toxicity in Mice

Employing a slightly modified version of the technique developed by Haley and McCormick (Brit. J. Pharmacol. 12: 12–15, 1957), young adult male and female Swiss mice received injections of a solution of the PRODUCT directly into lateral ventricles and brain tissue. Following injections the animals were observed for immediate reactions and then daily throughout a seven day observation period. The $LD_{50}$ values were calculated by the method of Litchfield and Wilcoxon (J. Pharmacol. Exp. Therap. 96: 99–113, 1949) with the following results.

| Concentration | $LD_{50}$/(95% Confidence Limits) | |
| (mg I/ml) | mg I/kg | mg/kg |
| --- | --- | --- |
| 350–450 | 1,640 (560–4806) | 3,985 (1,361–11,679) |

3. Acute Intracisternal Toxicity in Rats

A variation of the technique described by Melartin et al. (Invest. Radiol. 5: 13–21, 1970) was utilized to evaluate lethal effects of a solution of the PRODUCT after injection into cerebrospinal fluid at the cisterna magna. Young adult male and female Sprague Dawley rats were used. After dosing, the animals were housed individually and observed for immediate reactions and periodically for a two day observation period. The $LD_{50}$ values were calculated by the method of Litchfield and Wilcoxon (J. Pharmacol. Exp. Therap. 96: 99–113, 1949) with the following results.

| Concentration | $LD_{50}$/(95% Confidence Limits) | |
| (mg I/ml) | mg I/kg | mg/kg |
| --- | --- | --- |
| 400 | 550 (462–655) | 1,337 (1,123–1,592) |

4. Acute Intracisternal Neurotoxicity in Dogs

Adult dogs of either sex were employed for this procedure and were briefly anesthetized with thiopentol sodium during the injection of a solution of the PRODUCT. The compound was administered into cerebrospinal fluid at the cisterna magna at varying concentrations but at a constant 0.5 ml/kg volume dose. Animals were thereafter observed for neurotoxicity with the following results:

| Dosage Range (mg I/kg) | Minimum Convulsion Dose (mg I/kg) |
| --- | --- |
| 200–244 | >244* |

*Highest dose given at or below which no evidence of convulsive activity was observed. Respiratory arrest (death) occurred in 50% of the dogs at 244 mg I/kg.

What is claimed:

1. N-(2-Hydroxyethyl)-2,4,6-triiodo-3,5-bis-(2-keto-L-gulonamido)benzamide.

2. A radiological composition containing N-(2-hydroxyethyl)-2,4,6-triiodo-3,5-bis-(2-keto-L-gulonamido) benzamide in a sufficient amount to provide satisfactory x-ray visualization together with a pharmaceutically acceptable radiological vehicle.

3. In a method for x-ray visualization wherein a radiological composition containing an x-ray contrast agent in a pharmaceutically acceptable radiological vehicle is injected in a sufficient amount to provide adequate visualization and thereafter x-ray visualization carried out, the improvement comprising utilizing as the radiological composition a composition containing N-(2-hydroxyethyl)-2,4,6-triiodo-3,5-bis-(2-keto-L-gulonamido)benzamide in a sufficient amount to provide satisfactory x-ray visualization together with a pharmaceutically acceptable radiological vehicle.

4. N-(2-Acetoxyethyl)-3,5-bis-(2,3:4,6-di-O-isopropylidene-2-keto-L-gulonamido)-2,4,6-triiodobenzamide.

5. 3,5-Bis-(2,3:4,6-di-O-isopropylidene-2-keto-L-gulonamido)-N-(2-hydroxyethyl)-2,4,6-triiodobenzamide.

* * * * *